(12) United States Patent
Lee et al.

(10) Patent No.: US 7,799,907 B2
(45) Date of Patent: Sep. 21, 2010

(54) METHOD FOR THE PREPARATION OF 2'-DEOXY-2',2'-DIFLUOROCYTIDINE

(75) Inventors: Jaeheon Lee, Yongin-si (KR); Gha Seung Park, Yongin-si (KR); Moonsub Lee, Daejeon (KR); Hyo-Jeong Bang, Gunpo-si (KR); Jae Chul Lee, Suwon-si (KR); Cheol Kyong Kim, Suwon-si (KR); Chang-Ju Choi, Seoul (KR); Han Kyong Kim, Yongin-si (KR); Hoe Chul Lee, Yongin-si (KR); Young-Kil Chang, Seoul (KR); Gwan Sun Lee, Seoul (KR)

(73) Assignee: Hanmi Pharm. Co., Ltd, Kyungki-do (KR)

( * ) Notice: Subject to any disclaimer, the term of this patent is extended or adjusted under 35 U.S.C. 154(b) by 431 days.

(21) Appl. No.: 11/573,869

(22) PCT Filed: Dec. 29, 2005

(86) PCT No.: PCT/KR2005/004633

§ 371 (c)(1),
(2), (4) Date: Feb. 16, 2007

(87) PCT Pub. No.: WO2006/071090

PCT Pub. Date: Jul. 6, 2006

(65) Prior Publication Data

US 2007/0249818 A1   Oct. 25, 2007

(30) Foreign Application Priority Data

Dec. 30, 2004   (KR) ................ 10-2004-0116316
Jun. 23, 2005   (WO) ............... PCT/KR2005/001954

(51) Int. Cl.
  *C07H 19/073*   (2006.01)
(52) U.S. Cl. .................... 536/27.11; 536/28.5
(58) Field of Classification Search .......... None
  See application file for complete search history.

(56) References Cited

U.S. PATENT DOCUMENTS

| | | | |
|---|---|---|---|
| 4,965,374 A | 10/1990 | Chou et al. |
| 5,371,210 A | 12/1994 | Chou |
| 5,401,861 A | 3/1995 | Chou |
| 5,637,688 A | 6/1997 | Berglund |
| 5,744,597 A | 4/1998 | Chou |
| 5,945,547 A | 8/1999 | Chou |

FOREIGN PATENT DOCUMENTS

| EP | 0 577 303 A1 | 1/1994 |
|---|---|---|
| GB | 824654 | 12/1959 |
| WO | 96/16072 A1 | 5/1996 |

OTHER PUBLICATIONS

Russian Office Action dated Dec. 29, 2005.
Russian Office Action dated Feb. 21, 2008: with a complete English transtation.
Russian Office Action dated Jun. 10, 2008: with a complete English translation.

*Primary Examiner*—Lawrence E Crane
(74) *Attorney, Agent, or Firm*—Sughrue Mion, PLLC

(57) ABSTRACT

Provided is an improved method for stereoselectively preparing 2'-deoxy-2',2'-difluorocytidine of formula (I), which includes reacting a 1-halo ribofuranose compound with a nucleobase of formula (IV) in a solvent to obtain a nucleo side of formula (II) with removal of a silyl halide ((alkyl)$_3$SiX (X=halide)); and deprotecting the nucleoside of formula (II) to obtain 2'-deoxy-2',2'-difluorocytidine of formula (I). 2'-Deoxy-2',2'-difluorocytidine of formula (I) is effective for treating various cancers such as non-small cell lung (NSCLC), pancreatic, bladder, breast or ovarian cancers.

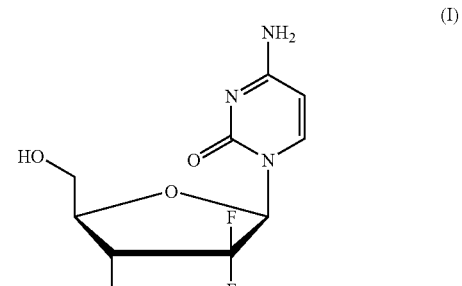

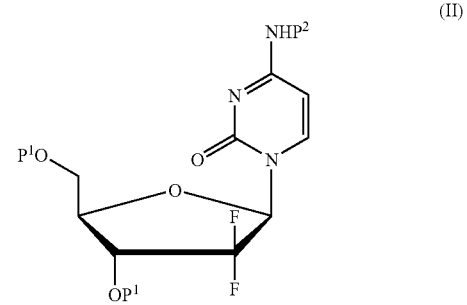

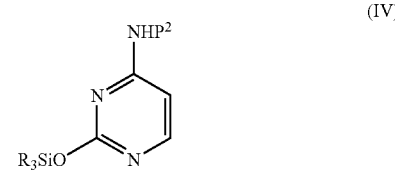

21 Claims, 3 Drawing Sheets

METHOD FOR THE PREPARATION OF 2'-DEOXY-2',2'-DIFLUOROCYTIDINE

This is a national stage application of PCT/KR05/04633 filed on Dec. 29, 2005, which claims priority from Korean patent application 10-2004-0116316 filed on Dec. 30, 2004, and PCT/KR05/01954 filed on Jun. 23, 2005, all of which are incorporated herein by reference.

FIELD OF THE INVENTION

The present invention relates to a method for stereoselectively preparing 2'-deoxy-2',2'-difluorocytidine.

DESCRIPTION OF THE PRIOR ART

2'-Deoxy-2',2'-difluorocytidine (Gemcitabine) of formula (I) has a cytosine nucleobase stereochemically-oriented to β-direction at the 1-position of the ribofuranose backbone, and is effective for treating various cancers such as non-small cell lung (NSCLC), pancreatic, bladder, breast or ovarian cancers.

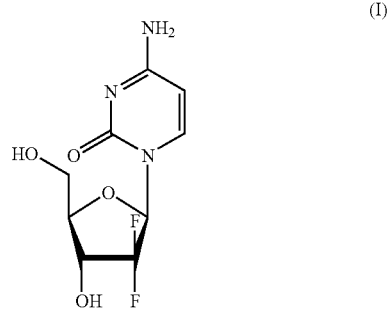

Gemcitabine can be conventionally prepared from a lactol compound as shown in Reaction Scheme 1 via an activated ribofuranose intermediate having a reactive leaving group.

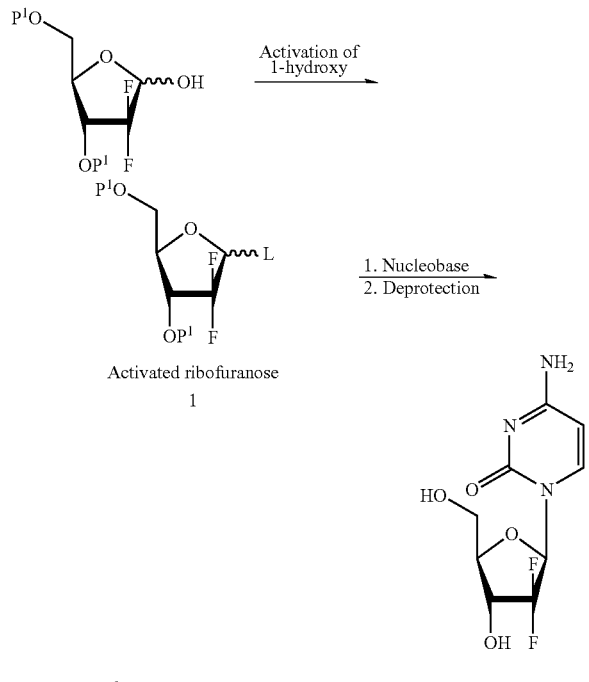

wherein, $P^1$ is a hydroxyl protecting group and L is a leaving group.

Examples of the activated ribofuranose intermediate for glycosylation are 1-sulfonate ribofuranose such as α-methanesulfonate ribofuranose and 1-halo ribofuranose.

The α-methanesulfonate ribofuranose may be reacted with a nucleobase to carry out stereoselective glycosylation to obtain the desired β-nucleosides in a high yield (See U.S. Pat. Nos. 5,371,210, 5,401,838, 5,426,183, 5,594,124 and 5,606,048 and EP Patent No. 577303). However, so as to produce α-methanesulfonate ribofuranose in a high ratio as compared with β-methanesulfonate ribofuranose, it is required to a cryogenic condition of below about −80° C., and thus, this method is not suitable for the mass production.

The 1-halo ribofuranose derivatives may be easily produced under a mild condition (e.g., room temperature) and reacted with an anionic nucleobase to carry out glycosylation (See U.S. Pat. No. 5,744,597 and EP Patent No. 577304). However, the glycosylation using a 1-halo ribofuranose derivative is non-stereoselective (i.e., anomerization at 1-position is occurred), leading to a mixture of α- and β-nucleosides and ultimately to a low yield of the desired β-nucleoside.

U.S. Pat. No. 5,223,608 discloses a process for selectively isolating the β-anomer of cytidinenucleoside from a 1:1 mixture of α- and β-cytidinenucleoside anomers by converting the mixture into the hydrochloride form, dissolving the hydrochloride mixture in hot water, adjusting pH of the resulting solution to 8.2, and cooling and filtering the solution. However, this process also give a low yield of the β-anomer.

The present inventors have endeavored to overcome the problems of the prior arts and found that an anomerization is effectively suppressed by removing the halide compound as it is generated during the glycosylation when 1-halo ribofuranose derivative is used and consequently the stereoselectivity can be markedly enhanced.

SUMMARY OF THE INVENTION

Accordingly, it is a primary object of the present invention to provide an improved method for preparing 2'-deoxy-2',2'-difluorocytidine in a high purity and yield under a new stereoselective glycosylation reaction using a 1-halo ribofuranose.

In accordance with the present invention, there is provided a method for preparing 2'-deoxy-2',2'-difluorocytidine of formula (I), which comprises the steps of (i) reacting a 1-halo ribofuranose compound of formula (III) with a nucleobase of formula (IV) in a solvent to obtain a nucleoside of formula (II) while continuously removing the silyl halide of formula (V) produced during the reaction; and (ii) deprotecting the nucleoside of formula (II) to obtain 2'-deoxy-2',2'-difluorocytidine of formula (I):

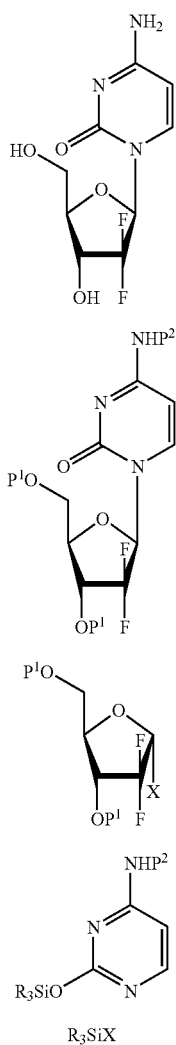

wherein,

R is alkyl;

$P^1$ is a hydroxy-protecting group;

$P^2$ is an amino-protecting group; and

X is halogen.

BRIEF DESCRIPTION OF THE DRAWINGS

The above and other objects and features of the present invention will become apparent from the following description of the invention taken in conjunction with the following accompanying drawings, which show.

DETAILED DESCRIPTION OF THE INVENTION

Figure 1:
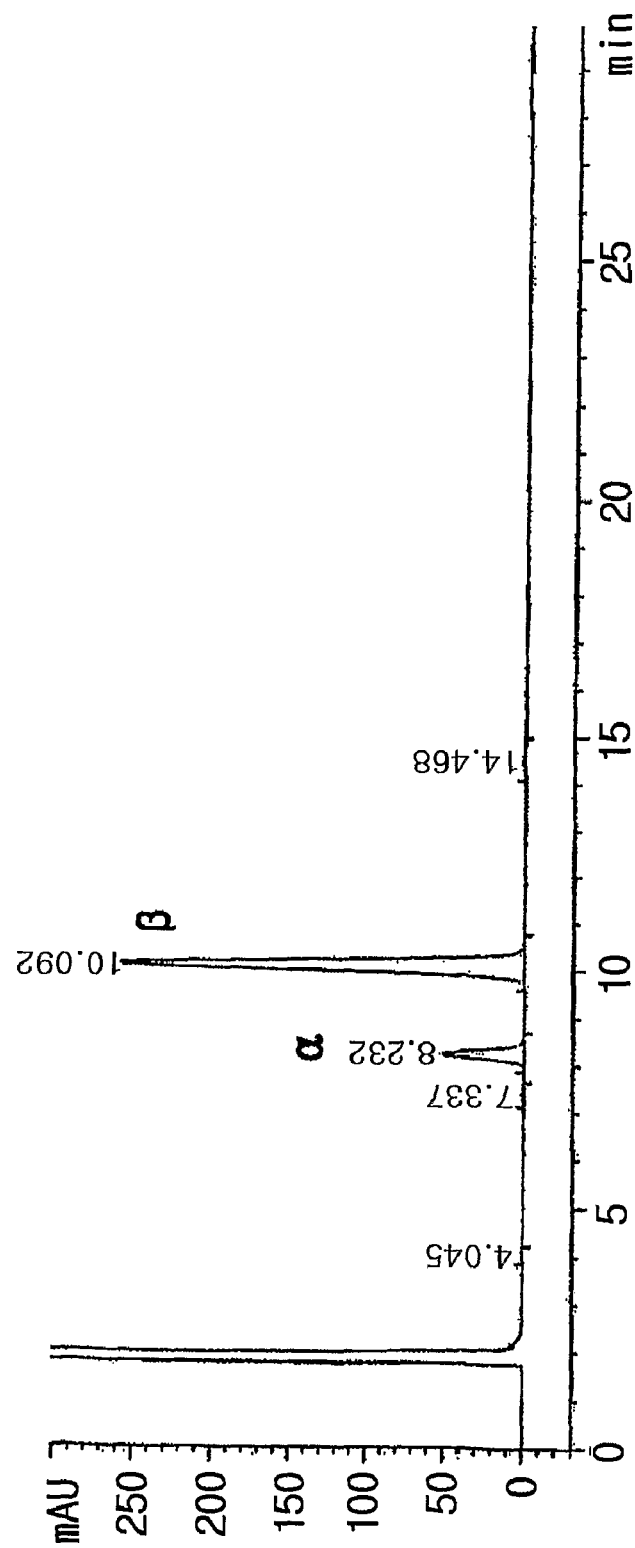
FIGS. 1 to 3: high pressure liquid chromatography (HPLC) scans of the compounds prepared in Example 4, Comparative Examples 1 and 2, respectively.

The inventive method is characterized that the compound of formula (I) can be efficiently prepared by continuously removing the silyl halide of formula (V) which is produced during the glycosylation.

The term "anomer-enriched" used herein means an anomer mixture having a specific anomer content of greater than 50%, including a substantially pure anomer. Also, the term "anomerization" means that a substantially pure anomer or a mixture of α-anomer and β-anomer is epimerized at the $C_1$-position of a ribofuranose.

The term "carrier" used herein means a solvent that is used to remove the silyl halide produced during the glycosylation and the term "heating medium" means a solvent of a high boiling point that can provide a sufficient heat to a reaction system and maintain the reaction mixture at a sufficiently high temperature to enable the continuous removal of the silyl halide by distillation.

The term "substituted" used herein means substitution alone or in combination by at least one or more of the groups selected from hydrogen, cyano, halo, carboalkoxy, toluoyl, nitro, alkoxy and alkyl.

In accordance with the present invention, the stereoselective glycosylation is carried out as shown in Reaction Scheme 2.

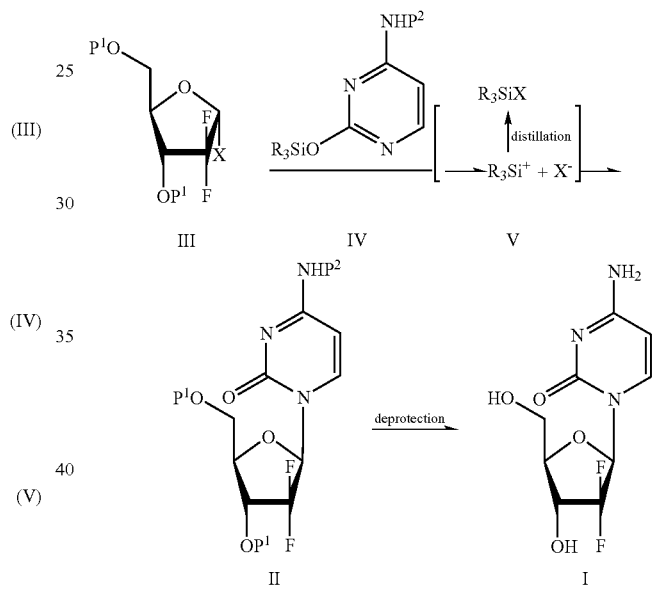

Specifically, an α-anomer enriched 1-halo ribofuranose of formula (III) is reacted with a nucleobase of formula (IV) for glycosylation to produce a β-nucleoside of formula (II) together with a silyl halide of formula (V) which may function as a halide source to bring about the anomerization of α-anomer. Accordingly, the silyl halide is continuously removed as it is formed by simple distillation or by using an inert gas until the glycosylation reaction is completed. As a result, the extent of anomerization is remarkably reduced and highly stereoselective glycosylation occurs in favor of the β-anomer.

The distillation is carried out with simultaneously adding a carrier or a mixture of a carrier and a heating medium which have a high boiling point dropwise to the reaction mixture for glycosylation.

Alternatively, the inert gas is passed through a separate tube which is inserted in a reactor to exhaust the silyl halide out of the reaction mixture without affecting the glycosylation reaction. The inert gas is introduced from the tube which is set up within (bubbling) or above (sweeping) the reacting solution for the removal of silyl halide.

The α-anomer enriched 1-halo ribofuranose of formula (III) used as a starting material in the inventive method has a hydroxy-protecting group, and can be prepared by the method described in Korean Patent Application No. 2004-59623. Exemplary hydroxy-protecting groups are formyl, acetyl, substituted acetyl, propionyl, butynyl, pivalamido, benzoyl, biphenylcarbonyl, substituted biphenylcarbonyl, ethoxycarbonyl, t-butoxycarbonyl, benzyloxycarbonyl, phenoxycarbonyl, benzyl, diphenylmethyl, triphenylmethyl, t-butyl, tetrahydropyranyl, allyl, N-phenylcarbamate, N-imidazoyl carbamate, trialkylsilyl, isopropyldialkylsilyl, alkyldiisopropylsilyl, triisopropylsilyl and t-butyldialkylsilyl. Among these, benzoyl, biphenylcarbonyl and substituted biphenylcarbonyl are more preferred.

The nucleobase of formula (IV) has an amino-protecting group, and it can be prepared by use of the methods described in U.S. Pat. Nos. 5,371,210, 5,401,838, 5,426,183, 5,594,124 and 5,606,048 and EP Patent No. 577303. Exemplary amino-protecting groups are silyl groups such as trimethylsilyl, triisopropylsilyl, tributylsilyl, t-butyldimethylsilyl and t-butyldiarylsilyl; carbamates such as t-butoxycarbonyl, benzyloxycarbonyl, 4-methoxybenzyloxycarbonyl and 4-nitrobenzyloxycarbonyl; formyl, acetyl, benzoyl and pivaloyl, methoxymethyl, t-butyl, benzyl and tetrahydropyranyl. Among these, trimethylsilyl is most preferred.

In the inventive method, the nucleobase of formula (IV) is used in an amount ranging from 5 to 50 molar equivalents, preferably 10 to 30 molar equivalents, more preferably 15 to 20 molar equivalents, based on the 1-halo ribofuranose of formula (III).

The solvents suitable for use in the present glycosylation process are benzene, substituted benzene, toluene, xylene, decalin, diglyme, 2-ethoxyethyl ether, diphenylether, substituted diphenylether, biphenyl, substituted biphenyl, $C_{6-14}$ alkane, substituted $C_{6-14}$ alkane and a mixture thereof. Among these, toluene, $C_{7-14}$ alkane, diphenylether and a mixture thereof are preferred, and a mixture of diphenylether and heptane is most preferred. The solvent is used in an amount ranging from 5 to 50 ml, preferably 10 to 20 ml based on 1 g of 1-halo ribofuranose of formula (III).

The carrier used to assist the removal of the silyl halide of formula (V) by distillation must be inert under the glycosylation reaction conditions and preferably has a boiling point higher than that of the silyl halide. The carrier may be benzene, substituted benzene, toluene, xylene, $C_{6-14}$ alkane, substituted $C_{6-14}$ alkane and a mixture thereof. Among these, toluene, heptane, octane and nonane are preferred, and heptane is most preferred. The carrier is used in an amount ranging from 50 to 1000 ml, preferably 100 to 300 ml based on 1 g of the 1-halo ribofuranose of formula (III).

In the inventive method, a heating medium having a high boiling point of 200° C. or higher may be further used in the form of a mixture with the carrier, so as to provide a reaction system with sufficient heat and complement the loss solvent due to distillation. The heating medium must be inert under the glycosylation reaction conditions and preferably has a boiling point higher than that of the carrier. The heating medium may be selected from the group consisting of decalin, diphenylether, substituted diphenylether, biphenyl, substituted biphenyl and a mixture thereof. Among these, diphenylether is most preferred. The heating medium is used in an amount ranging from 0.1 to 5 vol %, preferably 0.5 to 3 vol % based on the amount of the carrier.

It is preferred that the carrier and the heating medium are continuously added to the reaction mixture in a constant rate until the glycosylation reaction is completed, so as to obtain a uniform stereoselectivity.

In addition, a silyl source such as N,O-bis(trimethylsilyl)acetamide (BSA) may be further added in the form of a mixture with the carrier to the reaction mixture, so as to enhance the removal of the silyl halide by distillation. The silyl source may be used in an amount ranging from 0.05 to 1.5 vol %, preferably 0.1 to 0.5 vol % based on the amount of the carrier.

In the present invention, an inert gas such as nitrogen, helium, neon and argon, preferably nitrogen, may also be used in the removal of the silyl halide of formula (V). The inert gas is preferably introduced at a flow rate of 1 l/min or more based on 100 g of 1-halo ribofuranose compound of formula (III). When the inert gas is introduced at a flow rate less than 1 l/min, the ratio of β-nucleosides to α-nucleosides becomes not more than 3.

The glycosylation according to the present invention is carried out at a temperature ranging from 80 to 300° C., preferably 100 to 200° C., more preferably 130 to 150° C. for 4 to 24 hours.

The progress of the glycosylation may be checked by thin layer chromatography (TLC), $^1$H nucleus magnetic resonance ($^1$H-NMR) or high pressure liquid chromatography (HPLC).

The deprotection of the β-anomer enriched nucleoside of formula (II) may be carried out by a conventional method. For example, most silyl protecting groups are easily cleaved by the action of water or an alcohol. The acyl-amino protecting groups such as formyl, acetyl, pivaloyl and benzoyl are removed by hydrolysis with a strong base. Such bases include alkali metal hydroxides such as sodium or potassium hydroxide; alkali metal alkoxides such as sodium methoxide or potassium t-butoxide; diethylamine, hydroxylamine, ammonia, hydrazine and the like, among these, ammonia is preferred. Also, the acyl protecting groups can be removed using an acid catalyst such as methanesulfonic acid, hydrochloric acid, hydrobromic acid, sulfuric acid, or an acidic ion exchange resin.

β-Anomer enriched nucleoside of formula (II) may be obtained in a pure form by a separation based on solubility difference from a mixture of β-anomer enriched nucleoside of formula (II) and the unreacted cytosine as produced after the deprotection. The separation is preferably carried out by using the solvent system consisting of methylene chloride and methanol wherein β-anomer enriched nucleoside of formula (II) is highly soluble while the unreacted cytosine is sparingly soluble.

Thus, in accordance with the stereoselective glycosylation of the present invention, a β-enriched nucleoside product having an α:β ratio of 1:4 to 1:14 is obtained.

The β-nucleoside of formula (I) can be isolated in the form of hemihydrate or dihydrate in a high purity of 99.8% or more and a yield of 70% or more by a single recrystallization procedure which comprises dissolving the α/β anomer mixture in water, heating the mixture to a temperature of 40 to 60° C., cooling to 10 to 25° C. and filtering the solids precipitated during the cooling step. This procedure may be conducted with stirring when the hemihydrate form is derived or without stirring for the dihydrate form.

It has been proved that the hemihydrate or dihydrate form of the β-nucleoside obtained by the present invention is stable for the moisture content changes thereof under the conditions shown in Table 1.

TABLE 1

|  |  | Moisture content (%) | |
| --- | --- | --- | --- |
|  |  | Hemihydrate | Dihydrate |
| Air | 1 day | 3.6 | 11.6 |
|  | 7 days | 3.7 | 11.8 |
|  | 14 days | 3.4 | 11.7 |
| 40° C. under | 1 day | 3.7 | 12.1 |
| 75% relative | 7 days | 3.8 | 11.9 |
| humidity | 14 days | 3.8 | 11.7 |

Theoretical moisture content of Gemsitabine: Hemihydrate 3.3% dihydrate 12.0%

The highly pure hemihydrate or dihydrate of β-nucleosides can be directly used without further purification to prepare a pharmaceutically acceptable hydrochloride salt of the purity range described in pp 892-894 of U.S. Pharmacopoeia (2004).

Accordingly, the present invention also provides a method for preparing 2'-deoxy-2',2'-difluorocytidine hydrochloride comprising reacting 2'-deoxy-2',2'-difluorocytidine of formula (I) or a hemihydrate or dihydrate thereof with hydrochloric acid in an organic solvent.

The present invention will be described in further detail with reference to Examples. However, it should be understood that the present is not restricted by the specific Examples.

In Examples, —OCOBiPh or BiPhOCO— structurally means

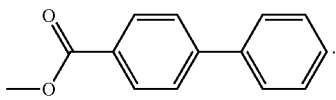

Also, each product obtained was analyzed by HPLC under two conditions: (1) Zorbax RX-C8 column (4.5×250 mm, 5 μm), NaH$_2$PO$_4$.H$_2$O 13.8 g/H$_2$PO$_4$ (pH 2.4-2.6) 2.5 ml dissolved in 1 l of water for the compound of formula (I); and (2) YMC hydrosphere C18 column (4.6×150 mm, 5 μm), a mixture of 760 ml of methanol and 240 ml of NaH$_2$PO$_4$.H$_2$O 13.8 g/H$_2$PO$_4$ (pH 2.4-2.6) 2.5 ml dissolved in 1 l of water for the compound of formula (II).

EXAMPLE

Preparation 1: Preparation of 1-α-bromo-2'-deoxy-2',2'-difluoro-D-ribofuranosyl-5-benzoyl-3-(4-phenyl)benzoate Step 1: Preparation of 2'-deoxy-2',2'-difluoro-D-ribofuranosyl-5-benzoyl-3-(4-phenyl)benzoate

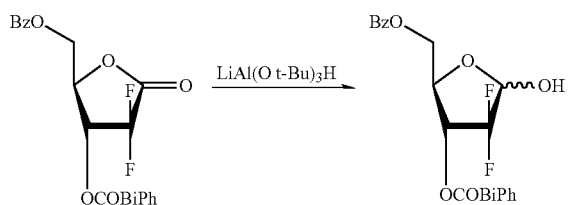

13.5 g of lithium tri-tert-butoxyaluminohydride was dissolved in 160 ml of teterahydrofuran, stirred at room temperature for 30 minutes and cooled to −40° C., to which 20 g of D-erythro-2-deoxy-2,2-difluoro-pentofuranos-1-ulose-5-benzoyl-3-(4-phenyl) dissolved in 80 ml of teterahydrofuran was added. The mixture was slowly warmed to room temperature and allowed to react at that temperature for 2 hours. Upon completing the reaction, 220 ml of 1N-HCl was added to the reaction mixture and the teterahydrofuran layer was separated. The aqueous layer was extracted with 220 ml of ether, combined with the pre-separated teterahydrofuran layer, washed successively with 220 ml portion of water, saturated sodium bicarbonate and brine, dried over magnesium sulfate and filtered. The solvent was removed under a reduced pressure and the residue was purified by silica gel column chromatography to obtain 18.3 g of the title compound (yield: 91%) as a light yellow syrup.

$^1$H-NMR (300 MHz, CDC$_{13}$, δ); 3.89-3.91 (d, 1H), 4.61-4.81 (m, 2H), 5.31-5.92 (m, 2H), 7.26-7.70 (m, 10H), 8.05-8.16 (m, 4H)

Step 2: Preparation of 2'-deoxy-2',2'-difluoro-D-ribofuranosyl-5-benzoyl-3-(4-phenyl)benzoate-1β-diphenylphosphate

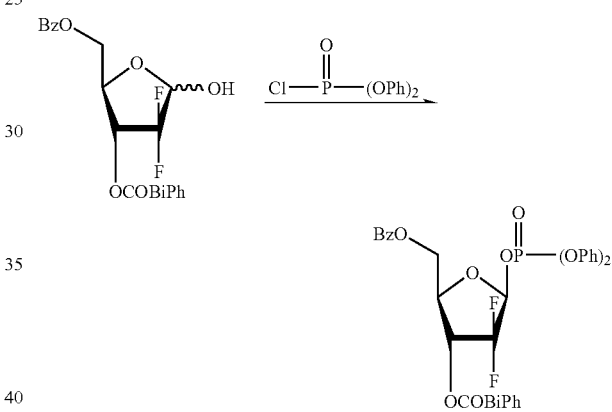

18.3 g of 2'-deoxy-2',2'-difluoro-D-ribofuranosyl-5-benzoyl-3-(4-phenyl)benzoate obtained in Step 1 was dissolved in 146 ml of toluene, 6.7 ml of triethylamine was added thereto, and 12.4 ml of diphenyl chlorophosphate diluted in 37 ml of toluene was added dropwise thereto. After 4 hours, 48 ml of 1N HCl was added to the reaction mixture to neutralize residual triethylamine, the toluene layer was separated and the aqueous layer was extracted with 48 ml of ether. The ether extract was combined with the pre-separated toluene layer and washed successively with water, saturated sodium bicarbonate and brine. The organic layer was separated, dried over magnesium sulfate and filtered. The solvent was removed under a reduced pressure to obtain a mixture of α- and β-phosphate as a solid. The mixture was examined by $^1$H-NMR analysis to find that the α-phosphate:β-phosphate ratio was 1:10.6. The β-phosphate was selectively recrystallized from a 3:1 (v/v) mixture of isopropanol and water, to obtain 26.5 g (yield: 87%) of the title compound as a white solid.

$^1$H-NMR (300 MHz, CDC$_{13}$, δ); 4.56-4.25 (m, 3H), 5.80 (m, 1H), 5.95 (t, 1H), 7.44-6.98 (m, 16H), 7.51 (d, 2H), 7.57 (d, 2H), 7.89 (d, 2H), 8.01 (d, 2H)

m.p: 101-103° C.

HPLC purity (area %): α-phosphate anomer 1.76%, β-phosphate anomer 98.24%

Step 3: Preparation of 1-α-bromo-2'-deoxy-2',2'-difluoro-D-ribofuranosyl-5-benzoyl-3-(4-phenyl)benzoate

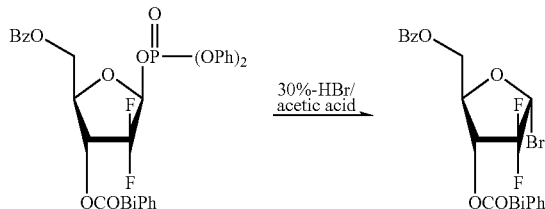

22.8 g of 2'-deoxy-2',2'-difluoro-D-ribofuranosyl-5-benzoyl-3-(4-phenyl)benzoate-1β-diphenylphosphate obtained in Step 2 was added to 80.5 ml of 30% HBr/acetic acid and the mixture was allowed to react at room temperature for 6 hours. The resulting solution was diluted with 400 ml of methylene chloride and 500 ml of ice water was slowly added thereto. The aqueous layer was removed and the methylene chloride layer was washed successively with ice water, saturated sodium bicarbonate and brine. The methylene chloride layer was dried over magnesium sulfate and filtered. The filtrate was concentrated under a reduced pressure to obtain a mixture of α- and β-isomers as a solid. The mixture was examined by $^1$H-NMR analysis to find that the α-bromo:β-bromo ratio was 10.7:1. The β-bromo compound was selectively recrystallized from isopropanol to obtain 17.0 g (yield: 82%) of the title compound as a white solid.

$^1$H-NMR (300 MHz, CDC$_{13}$, δ); 8.19 (d, 2H), 8.06 (d, 2H), 7.73 (d, 2H), 7.63 (d, 2H), 7.64-7.41 (m, 6H), 6.56 (d, 1H), 5.60 (dd, 1H)

m.p: 111-112° C.

HPLC purity (area %): α-bromo anomer 99.74%, β-bromo anomer 0.26%

Preparation 2: Preparation of 1-α-bromo-2'-deoxy-2',2'-difluoro-D-ribofuranosyl-3,5-di-(4-phenyl)benzoate

Step 1: Preparation of 2'-deoxy-2',2'-difluoro-D-ribofuranosyl-3,5-di-(4-phenyl)benzoate

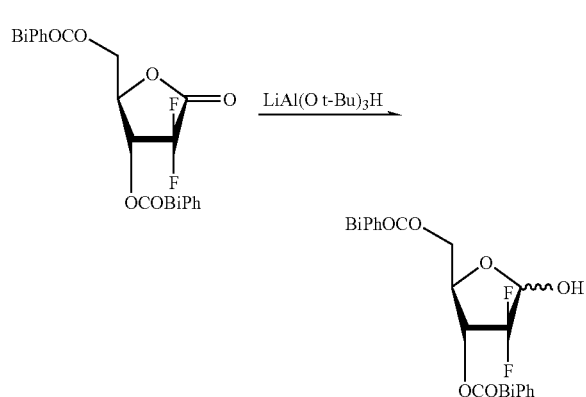

8.66 g of lithium tri-tert-butoxyaluminohydride was dissolved in 120 ml of teterahydrofuran, stirred at room temperature for 30 minutes and cooled to −40° C., to which 15 g of D-erythro-2-deoxy-2,2-difluoro-pentofuranos-1-ulose-3,5-di-(4-phenyl) dissolved in 100 ml of teterahydrofuran was slowly added. The mixture was then heated to room temperature and allowed to react for 1 hour. 142 ml of 1N-hydrochloric acid was slowly added dropwise to the reaction mixture to decompose excess lithium tri-tert-butoxyaluminohydride, and the organic layer was separated. The aqueous layer was extracted with 150 ml of ether, combined with the pre-separated organic layer, washed successively with 220 ml of water, saturated sodium bicarbonate and brine, dried over magnesium sulfate and filtered. The solvent was removed under a reduced pressure and the resulting solid was recrystallized from toluene to obtain 13.4 g of the title compound (yield: 89%) as a white solid.

$^1$H-NMR (300 MHz, CDC$_{13}$, δ); 3.45 (s, 1H), 4.85-4.50 (m, 3H), 5.8-5.4 (m, 2H), 7.49-7.43 (m, 6H), 7.71-7.61 (m, 8H), 8.18-8.12 (m, 4H)

m.p: 156-158° C.

Step 2: Preparation of 2'-deoxy-2',2'-difluoro-D-ribofuranosyl-3,5-di-(4-phenyl)benzoyl-1β-diphenylphosphate

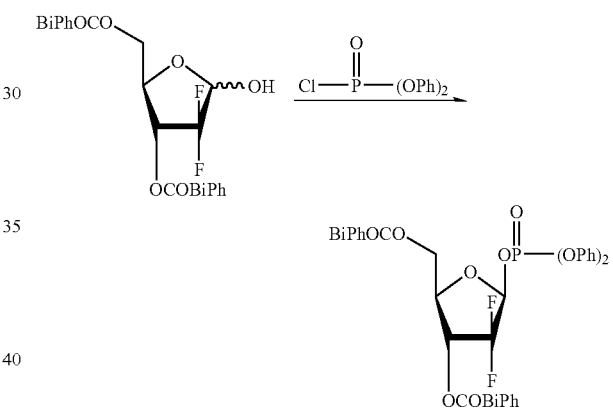

13 g of 2'-deoxy-2',2'-difluoro-D-ribofuranosyl-3,5-(4-phenyl) benzoate obtained in Step 1 was dissolved in a mixture of 130 ml of toluene and 100 ml of methylene chloride, and 5.1 ml of triethylamine was added thereto. 7.6 ml of diphenyl chlorophosphate was added dropwise to the mixture at room temperature. After 5 hours, the solvent was removed under a reduced pressure, the resulting solid was dissolved in 130 ml of methylene chloride, and 65 ml of 1N HCl was added thereto. The organic layer was separated, washed successively with water, saturated sodium bicarbonate and brine, dried over magnesium sulfate and filtered. The solvent was removed under a reduced pressure to obtain a mixture of α- and β-phosphate as a solid. The mixture was examined by $^1$H-NMR analysis to find that the α-phosphate:β-phosphate ratio was 1:10.8. The β-phosphate was selectively recrystallized from isopropanol to obtain 15 g (yield: 83%) of the title compound as a white solid.

$^1$H-NMR (300 MHz, CDC$_{13}$, δ); 4.70-4.40 (m, 3H), 5.90 (m, 1H), 6.08 (t, 1H), 7.70-7.08 (m, 24H), 8.15-8.04 (dd, 4H)

m.p: 145-147° C.

HPLC purity (area %): α-phosphate anomer 1.29%, β-phosphate anomer 98.71%

Step 3: Preparation of 1-α-bromo-2'-deoxy-2',2'-difluoro-D-ribofuranosyl-3,5-di-(4-phenyl)benzoate

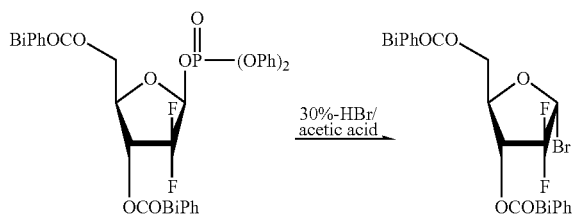

13 g of 2'-deoxy-2',2'-difluoro-D-ribofuranosyl-3,5-di-(4-phenyl)benzoyl-1β-diphenylphosphate obtained in Step 2 was added to 83.2 ml of 30% HBr/acetic acid and the mixture was allowed to react at room temperature for 7 hours. 50 ml of ice water was slowly added to the reaction solution and the solid formed was filtered. The filtered solid was a mixture of α- and β-bromo and a $^1$H-NMR analysis showed that the α-bromo:β-bromo ratio was 10.9:1. The α-bromo compound was selectively recrystallized from ethanol to obtain 8.45 g (yield: 83%) of the title compound as a white solid.

$^1$H-NMR (300 MHz, $CDC1_3$, δ); 4.89-4.22 (m, 3H), 5.62 (dd, 1H), 6.55 (d, 1H), 7.73-7.42 (m, 14H), 8.63-8.11 (dd, 4H) m.p: 151-153° C.

HPLC purity (area %): α-bromo anomer 99.67%, β-bromo anomer 0.33%

Example 1

1-(2'-Deoxy-2',2'-difluoro-5-benzoyl-3-(4-phenyl)benzoyl-D-ribofuranosyl-4-aminopyrimidin-2-one

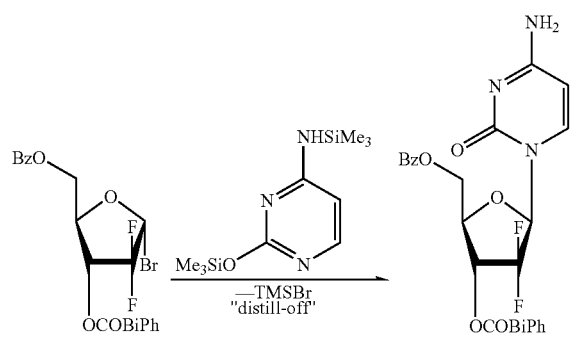

Example 1-1

44.5 g of cytosine, 252 ml of hexamethyldisilazane and 252 mg of ammonium sulfate were mixed and refluxed until the solution became homogeneous, which was further refluxed for 1 hour. 200 ml of ethyl acetate was added thereto and heated to remove remaining unreacted hexamethyldisilazane. A mixture of 160 ml of heptane and 40 ml of diphenylether and 10.4 g of 1-α-bromo-2'-deoxy-2',2'-difluoro-D-ribofuranosyl-5-benzoyl-3-(4-phenyl)benzoate obtained in Preparation 1 were added to the resulting solution. The resulting mixture was reacted for 8 hours while adding dropwise a diphenylether (40 ml)/heptane (4 l) mixture thereto and at the same time carrying out distillation with maintaining the reaction temperature at 130 to 140° C. This procedure allowed continuous removal of trimethylsilyl bromide from the reaction mixture during the course of the reaction. After completing the reaction, 140 ml of heptane was added to the reaction mixture. The solution was cooled to 100° C., carefully quenched with 12 ml of water and stirred at room temperature. The solid formed was filtered and washed with heptane to obtain a mixture of α- and β-nucleoside isomers including unreacted cytosine in the form of a white solid. The nucleoside mixture was examined by HPLC analysis to find that the α-nucleoside:β-nucleoside ratio was 1:8.8. The solid containing the nucleoside mixture and unreacted cytosine was added to a mixture of methylene chloride (200 ml) and methanol (40 ml), refluxed for 1 hour and filtered to remove cytosine. The filtrate was distilled under a reduced pressure, isopropylether was added to the residue, filtered and the filtrate was dried with warm wind to obtain 10.8 g (yield: 98%) of the title compound as a white solid.

$^1$H-NMR (300 MHz, DMSO, d-6, δ); 8.1 (d, 2H), 7.9 (d, 2H), 7.8 (d, 2H), 7.7 (d, 2H), 7.6 (d, 2H), 7.5-7.4 (m, 7H), 6.3 (t, 1H), 5.8 (m, 1H), 5.7 (d, 1H), 4.7-4.6 (m, 3H)

An anomer ratio (HPLC analysis): α-nucleoside/β-nucleoside=1/8.8

Example 1-2

11.1 g of cytosine, 63 ml of hexamethyldisilazane and 63 mg of ammonium sulfate were mixed and refluxed for 2 hours. 60 ml of toluene was added to the resulting mixture and heated to remove remaining unreacted hexamethyldisilazane. A mixture of 40 ml of octane and 20 ml of diphenylether and 3.5 g of 1-α-bromo-2'-deoxy-2',2'-difluoro-D-ribofuranosyl-5-benzoyl-3-(4-phenyl)benzoate obtained in Preparation 1 were added to the resulting solution. The resulting mixture was reacted for 10 hours while adding dropwise a diphenylether (10 ml)/heptane (1 l) mixture thereto and at the same time carrying out distillation with maintaining the reaction temperature at 140 to 150° C. This procedure allowed continuous removal of trimethylsilyl bromide from the reaction mixture during the course of the reaction. After completing the reaction, 50 ml of heptane was added to the reaction mixture. The solution was cooled to 80 to 100° C., carefully added dropwise 12 ml of water and the mixture was stirred at room temperature for 1 hour. The solid formed was filtered and washed with heptane to obtain a mixture of α- and β-nucleoside isomers including unreacted cytosine in the form of a white solid. The nucleoside mixture was examined by HPLC analysis to find that the α-nucleoside:β-nucleoside ratio was 1:5.6. The solid containing the nucleoside mixture and unreacted cytosine was added to a mixture of methylene chloride (70 ml) and methanol (15 ml), refluxed for 1 hour and filtered to remove cytosine. The filtrate was distilled under a reduced pressure, isopropyl ether was added to the residue, filtered and the filtrate was dried with warm wind to obtain 3.45 g (yield: 93%) of the title compound as a white solid.

H-NMR data was the same as in Example 1-1.

An anomer ratio (HPLC analysis): α-nucleoside/β-nucleoside=1/5.6

Example 1-3

2.23 g of cytosine, 12.6 ml of hexamethyldisilazane and 12.6 mg of ammonium sulfate were mixed and refluxed until the solution became homogeneous, which was further refluxed for 1 hour. 200 ml of ethyl acetate was added thereto and heated to remove remaining unreacted hexamethyldisilazane. 0.26 g of 1-α-bromo-2'-deoxy-2',2'-difluoro-D-ribofuranosyl-5-benzoyl-3-(4-phenyl)benzoate obtained in Preparation 1 was added to the resulting solution. The resulting mixture was reacted for 6 hours while adding N,O-bis(trimethylsilyl)acetamide (2 ml)/heptane (200 ml) mixture dropwise and at the same time carrying out distillation with maintaining the reaction temperature at 125 to 140° C. This procedure allowed continuous removal of trimethylsilyl bromide from the reaction mixture during the course of the reaction. After completing the reaction, the solution was cooled to 80° C., carefully added dropwise 1 ml of water and the mixture was stirred at room temperature for 1 hour. The solid formed was filtered and washed with heptane to obtain a mixture of α- and β-nucleoside isomers including unreacted cytosine in the form of a white solid. The nucleoside mixture was examined by HPLC analysis to find that the α-nucleoside:β-nucleoside ratio was 1:14.

Example 1-4

340 g of cytosine, 1.835 l of hexamethyldisilazane and 1.84 g of ammonium sulfate were mixed and refluxed until the solution became homogeneous, which was further refluxed for 1 hour. 1.2 l of heptane and 500 ml of diphenyl ether were successively added to the resulting solution to lower the temperature of the solution to 100° C. Next, 100 g of 1-α-bromo-2'-deoxy-2',2'-difluoro-D-ribofuranosyl-5-benzoyl-3-(4-phenyl) benzoate obtained in Preparation 1 was added thereto. The resulting mixture was reacted for 12 hours while inserting a separate tube in the reactor and introducing nitrogen at a flow of 1.0 to 1.3 l/min by sweeping thereto with maintaining the reaction temperature at 140 to 143° C. This procedure allowed continuous removal of trimethylsilyl bromide from the reaction mixture during the course of the reaction. After completing the reaction, the solution was cooled to 80° C. and 100 ml of water was carefully added thereto dropwise. The mixture was stirred at room temperature for 1 hour. The solid formed was filtered and washed with heptane to obtain a mixture of α- and β-nucleoside isomers including unreacted cytosine in the form of a white solid. The nucleoside mixture was examined by HPLC analysis to find that the α-nucleoside:β-nucleoside ratio was 1:4.9.

Example 1-5

The procedure of Example 1-4 was repeated except that nitrogen was introduced into the tube at a flow rate of 3.0 to 3.5 l/min, to obtain a mixture of α- and β-nucleoside isomers including unreacted cytosine in the form of a white solid. The nucleoside mixture was examined by HPLC analysis to find that the α-nucleoside:β-nucleoside ratio was 1:6.1.

Example 2

1-(2'-Deoxy-2',2'-difluoro-3,5-di-(4-phenyl)benzoyl-D-ribofuranosyl-4-aminopyrimidin-2-one

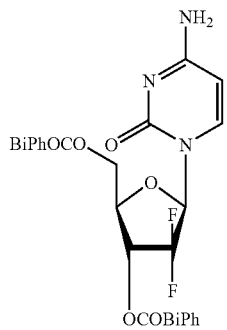

-continued

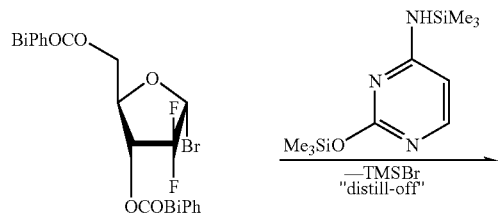

22.2 g of cytosine, 126 ml of hexamethyldisilazane and 126 mg of ammonium sulfate were mixed and refluxed for 2 hours, and 100 ml of ethyl acetate was added to remove unreacted hexamethyldisilazane by distillation. 80 ml of heptane, 5.93 g of 1-α-bromo-2'-deoxy-2',2'-difluoro-D-ribofuranosyl-3,5-di-(4-phenyl)benzoate obtained in Preparation 2 and 20 ml of diphenylether were successively added to the resulting solution. The resulting mixture was allowed to react for 9 hours while adding dropwise 4 l of heptane thereto and at the same time carrying out distillation with maintaining the reaction temperature at 130 to 140° C. This procedure allowed continuous removal of trimethylsilyl bromide from the reaction mixture during the course of the reaction. After completing the reaction, 160 ml of heptane was added to the reaction mixture. The solution was cooled to 100° C. and 8 ml of water was carefully added dropwise thereto. The solution was stirred at room temperature and filtered. The solid formed was washed with heptane to obtain a mixture of α- and β-nucleoside isomers including unreacted cytosine in the form of a white solid. The nucleoside mixture was examined by HPLC analysis to find that the α-nucleoside:β-nucleoside ratio was 1:5.4. The solid containing nucleoside mixture and the unreacted cytosine was added to a mixture of methylene chloride (200 ml) and methanol (40 ml), refluxed for 1 hour and filtered to remove cytosine. The filtrate was distilled under a reduced pressure to obtain 4 g (yield: 64%) of the title compound as a white solid.

$^1$H-NMR (300 MHz, $CDC_{13}$, δ): 8.74-7.27 (m, 19H), 6.38 (m, 1H), 5.83 (m, 1H), 5.78 (d, 1H), 4.78-4.45 (m, 3H)
m.p: 250-255° C.
An anomer ratio (HPLC analysis): α-nucleoside/β-nucleoside=1/5.4

Example 3

2'-Deoxy-2',2'-difluorocytidine (Compound of formula (I)-1: Gemcitabine)

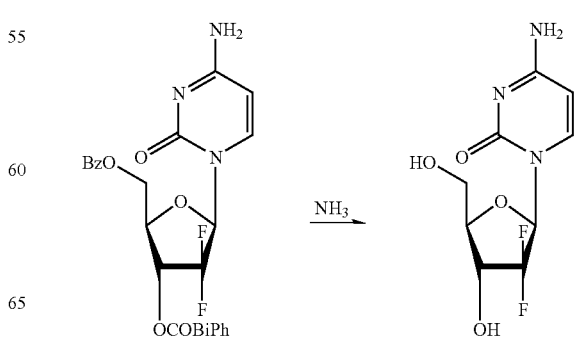

Example 3-1

2'-Deoxy-2',2'-difluorocytidine hemihydrate 10.8 g of 1-(2'-Deoxy-2',2'-difluoro-5-benzoyl-3-(4-phenyl)benzoyl-D-ribofuranosyl-4-aminopyrimidin-2-one obtained in Example 1-1 was added to 86 ml of 7N-ammonia in methanol and 216 ml of methanol was further added thereto. The mixture was stirred at room temperature for 12 hours and the solvent was removed under a reduced pressure. 120 ml of water and 80 ml of ethyl acetate were added to the mixture with stirring. The aqueous layer was separated and the ethyl acetate layer was extracted with 40 ml of water. The aqueous layers were combined, washed with 40 ml of diethyl ether and distilled under a reduced pressure to remove water. 25 ml of water was added to the resulting residue, the mixture was heated to 45 to 50° C. to dissolve the solid, cooled and stirred at room temperature for 2 hours to allow the precipitation of a solid. The solid was filtered, washed with water and acetone and dried with warm wind overnight to obtain 3.99 g (yield: 76.9%) of the title compound in the form of pure white hemihydrate.

Moisture content: 3.4%

$^1$H-NMR (300 MHz, DMSO d-6, δ); 7.7 (1H, d), 7.39 (1H, d), 6.2 (1H, d), 6.1 (1H, t), 5.8 (1H, t), 4.2 (m, 1H), 3.9-3.8 (m, 2H), 3.7 (m, 1H)

m.p.=198-202° C.

HPLC purity (area %): β-anomer—99.97%

α-anomer—less than 0.02% cytosine—less than 0.01%

Example 3-2

2'-Deoxy-2',2'-difluorocytidine dihydrate

The procedure of Example 3-1 was repeated except that the solution was cooled without stirring during the precipitation of solid, to obtain 4.22 g (yield: 81.3%) of the title compound in the form of pure white dihydrate.

Moisture content: 11.5% m.p.=220-224° C.

H-NMR data was the same as in Example 3-1.

HPLC purity (area %): β-anomer—99.98%,

α-anomer—less than 0.01% cytosine—less than 0.01%

Example 4

2'-Deoxy-2',2'-difluorocytidine (Compound of formula (I)-2: Gemicitabine)

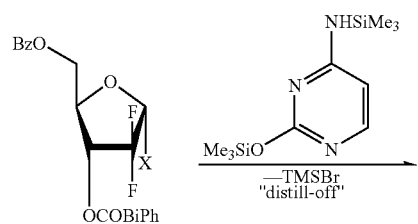

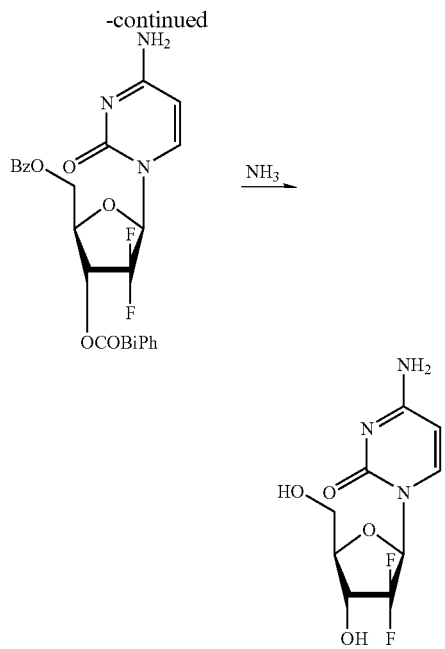

32.2 g of cytosine and 184 mg of ammonium sulfate were added to 184 ml of hexamethyldisilazane. The mixture was refluxed for 1 hour and 250 ml of heptane was added thereto and heated to 135 to 140° C. to distil off unreacted hexamethyldisilazane. 150 ml of heptane and 10.0 g of 1-α-bromo-2'-deoxy-2',2'-difluoro-D-ribofuranosyl-5-benzoyl-3-(4-phenyl)benzoate obtained in Preparation 1 were added to the resulting solution and then 38.7 ml of diphenylether was added thereto. The resulting mixture was allowed to react for 10 hours while adding dropwise 1.5 l of heptane thereto and at the same time carrying out distillation with maintaining the reaction temperature at 135 to 140° C. This procedure allowed continuous removal of trimethylsilyl bromide from the reaction mixture during the course of the reaction. After completing the reaction, 240 ml of heptane was added to the resulting solution and 11.6 ml of water was slowly added thereto. The solid formed was stirred, filtered, washed with heptane and dried at room temperature, to obtain a mixture of α- and β-nucleoside isomers including unreacted cytosine in the form of a white solid. The nucleoside mixture was examined by HPLC analysis to find that the α-nucleoside:β-nucleoside ratio was 1:6.1 (See FIG. 1). The solid was suspended in 300 ml of methylene chloride and 60 ml of methanol solution, and refluxed for 2 hours. The resulting mixture was filtered, the filtered solid was washed with a mixture of methylene chloride (150 ml) and methanol (30 ml) and distilled under a reduced pressure, to obtain an α/β mixture of 1-(2'-deoxy-2',2'-difluoro-5-benzoyl-3-(4-phenyl)benzoyl-D-ribofuranosyl-4-aminopyrimidin-2-one. The residue solid was added with 200 ml of methanol and 83 ml of 7N-ammonia/methanol solution, and stirred at room temperature overnight. After completing the reaction, the solvent was removed under a reduced pressure, and 80 ml of ethyl acetate and 90 ml of water were added to the residue. The aqueous layer was separated and the ethyl acetate layer was extracted with 40 ml of water. The aqueous layers were combined and washed with 40 ml of ether (×2). The water was distilled off under a reduced pressure until water was left in the amount of 5 times based on the theoretical weight of the desired product, and the residue was heated to 50 to 55° C.

and cooled to room temperature with stirring for 2 hours to induce the precipitation of a solid. The precipitated solid was filtered, washed with water and acetone and dried with warm wind overnight, to obtain 3.69 g (yield: 72.6%) of the title compound in the form of a pure white crystal.

Moisture content: 3.5%

H-NMR data and melting point were the same as in Example 3-1.

HPLC purity (area %): β-anomer—99.9%,
α-anomer—less than 0.01%
cytosine—less than 0.02%

Example 5

2'-Deoxy-2',2'-difluorocytidine (Compound of formula (I)-3: Gemicitabine)

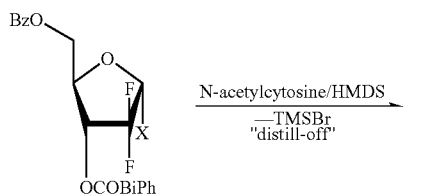

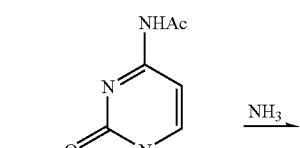

24 g of N-acetylcytosine and 126 ml of hexamethyldisilazane and 126 mg of ammonium sulfate were mixed and refluxed for 2 hours. 100 ml of heptane was added to the mixture and unreacted hexamethyldisilazane was removed by distillation. 50 ml of octane and 5 g of 1-α-bromo-2'-deoxy-2',2'-difluoro-D-ribofuranosyl-5-benzoyl-3-(4-phenyl)benzoate obtained in Preparation 1 were added to the resulting solution. The mixture was reacted for 8 hours while adding dropwise N,O-bis(trimethylsilyl)acetamide(1.8 ml)/heptane (900 ml) solution thereto and at the same time carrying out distillation with maintaining the reaction temperature at 135 to 140° C. This procedure allowed continuous removal of trimethylsilyl bromide from the reaction mixture during the course of the reaction. After completing the reaction, 60 ml of heptane was added to the resulting solution which was cooled to 100° C. and 12 ml of water was slowly added thereto. The solid formed was stirred at room temperature for 2 hours, filtered and washed with heptane, to obtain a mixture of α- and β-nucleoside isomers including unreacted cytosine in the form of a white solid. The nucleoside mixture was examined by HPLC analysis to find that the α-nucleoside:β-nucleoside ratio was 1:4.8. The nucleoside mixture was suspended in 108 ml of methanol and 45 ml of 7N ammonia/methanol solution, the solvent was removed under a reduced pressure, and 50 ml of ethyl acetate and 60 ml of water were added to the residue. The aqueous layer was separated and the ethyl acetate layer was extracted with 20 ml of water. The aqueous layers were combined and washed with 40 ml of ether (×2). Water was distilled off under a reduced pressure, and 15 ml of water was added to the residue which was heated to 50 to 55° C. and cooled to room temperature with stirring for 2 hours to induce the precipitation of a solid. The precipitated solid was filtered, washed with water and acetone and dried with warm wind overnight, to obtain 32.2 g (yield: 63%) of the title compound in the form of a pure white crystal.

H-NMR data and melting point were the same as in Example 3-1.

HPLC purity (area %): β-anomer—99.8%,
α-anomer—less than 0.02%
cytosine—less than 0.02%

Example 6

Hydrochloride of 2'-deoxy-2',2'-difluorocytidine

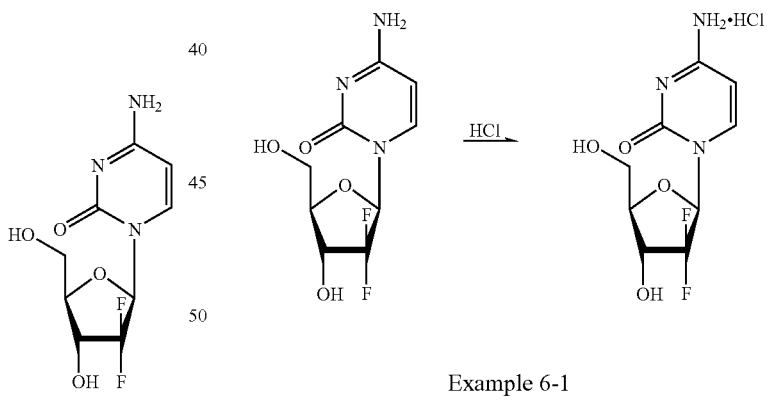

Example 6-1

3.5 g of 2'-Deoxy-2',2'-difluorocytidine hemihydrate (moisture content: 3.8%) obtained in Example 3-1 was dissolved in 35 ml of acetone and 1.2 ml of concentrated hydrochloric acid was added dropwise thereto. The resulting mixture was stirred at room temperature for 2 hours. The solid formed was filtered, washed with acetone and dried with warm wind to obtain 3.52 g (yield: 91.9%) of the title compound in the form of a pure white crystal.

$^1$H-NMR (300 MHz, DMSO, d6): 9.95 (s, 1H), 8.81 (s, 1H), 8.05 (d, 1H), 6.15 (d, 1H), 5.96 (m, 1H), 4.14-4.03 (m, 1H), 3.79 (d, 1H), 3.70-3.51 (m, 2H)

m.p: 287-292° C.

Example 6-2

3.5 g of 2'-Deoxy-2',2'-difluorocytidine dihydrate (moisture content: 11.5%) obtained in Example 3-2 was dissolved in 35 ml of acetone and 1.2 ml of concentrated hydrochloric acid was added dropwise thereto. The resulting mixture was stirred at room temperature for 2 hours. The solid formed was filtered, washed with acetone and dried with warm wind to obtain 3.23 g (yield: 91.5%) of the title compound in the form of a pure white crystal.

H-NMR data and melting point were the same as in Example 6-1.

COMPARATIVE EXAMPLE

Preparation of 2'-Deoxy-2',2'-difluorocytidine without the distillation for removing silyl halide

Comparative Example 1

Figure 2:
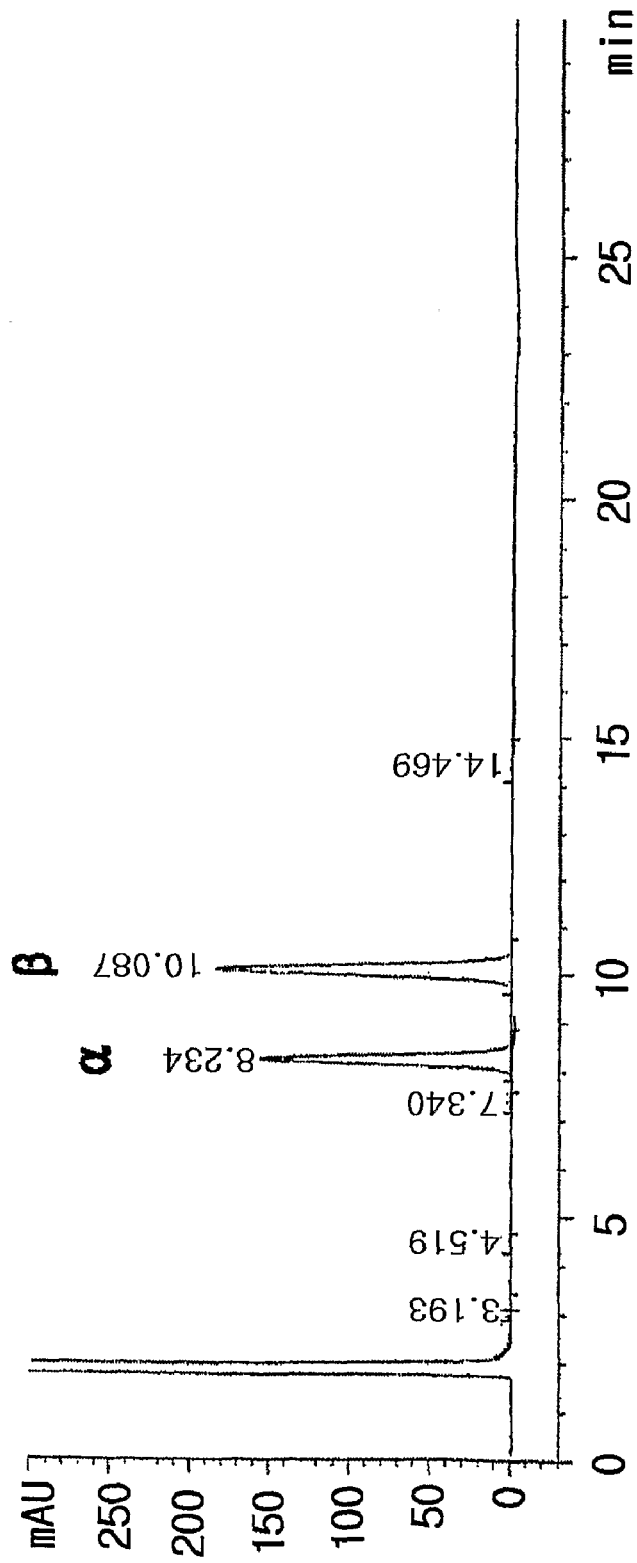

32.2 g of cytosine and 184 mg of ammonium sulfate were added to 184 ml of hexamethyldisilazane. The mixture was refluxed for 1 hour and 250 ml of heptane was added thereto and heated to 135 to 140° C. to distil off unreacted hexamethyldisilazane. 150 ml of heptane and 10.0 g of 1-α-bromo-2'-deoxy-2',2'-difluoro-D-ribofuranosyl-5-benzoyl-3-(4-phenyl)benzoate obtained in Preparation 1 were added to the resulting solution and then 38.7 ml of diphenylether was added thereto. The resulting mixture was allowed to react for 10 hours with refluxing and maintaining the reaction temperature at 135 to 140° C. After completing the reaction, 240 ml of heptane was added to the resulting solution and 11.6 ml of water was slowly added thereto. The solid formed was stirred, filtered, washed with heptane and dried at room temperature, to obtain a mixture of α- and β-nucleoside isomers including unreacted cytosine in the form of a white solid. The nucleoside mixture was examined by HPLC analysis to find that the α-nucleoside:β-nucleoside ratio was 1:1.4 (See FIG. 2). The solid was suspended in 300 ml of methylene chloride and 60 ml of methanol solution, and refluxed for 2 hours. The resulting mixture was filtered, the filtered solid was washed with a mixture of methylene chloride (150 ml) and methanol (30 ml) and distilled under a reduced pressure, to obtain an α/β mixture of 1-(2'-deoxy-2',2'-difluoro-5-benzoyl-3-(4-phenyl)benzoyl-D-ribofuranosyl-4-aminopyrimidin-2-one. The mixture was added with 200 ml of methanol and 83 ml of 7N-ammonia/methanol solution, and stirred at room temperature overnight. After completing the reaction, the solvent was removed under a reduced pressure, and 80 ml of ethyl acetate and 90 ml of water were added to the residue. The aqueous layer was separated and the ethyl acetate layer was extracted with 40 ml of water. The aqueous layers were combined and washed with 40 ml of ether (×2). The water was distilled off under a reduced pressure until water was left in the amount of 5 times based on the theoretical weight of the desired product, and the residue was heated to 50 to 55° C. and cooled to room temperature with stirring for 2 hours to induce the precipitation of a solid. The precipitated solid was filtered, washed with water and acetone and dried with warn wind overnight, to obtain 1.80 g (yield: 35.5%) of the title compound in the form of a pure white crystal.

Moisture content: 3.7%

H-NMR data and melting point were the same as in Example 3-1.

An anomer ratio (HPLC analysis): α-nucleoside/β-nucleoside=1/1.4

Comparative Example 2

Figure 3:
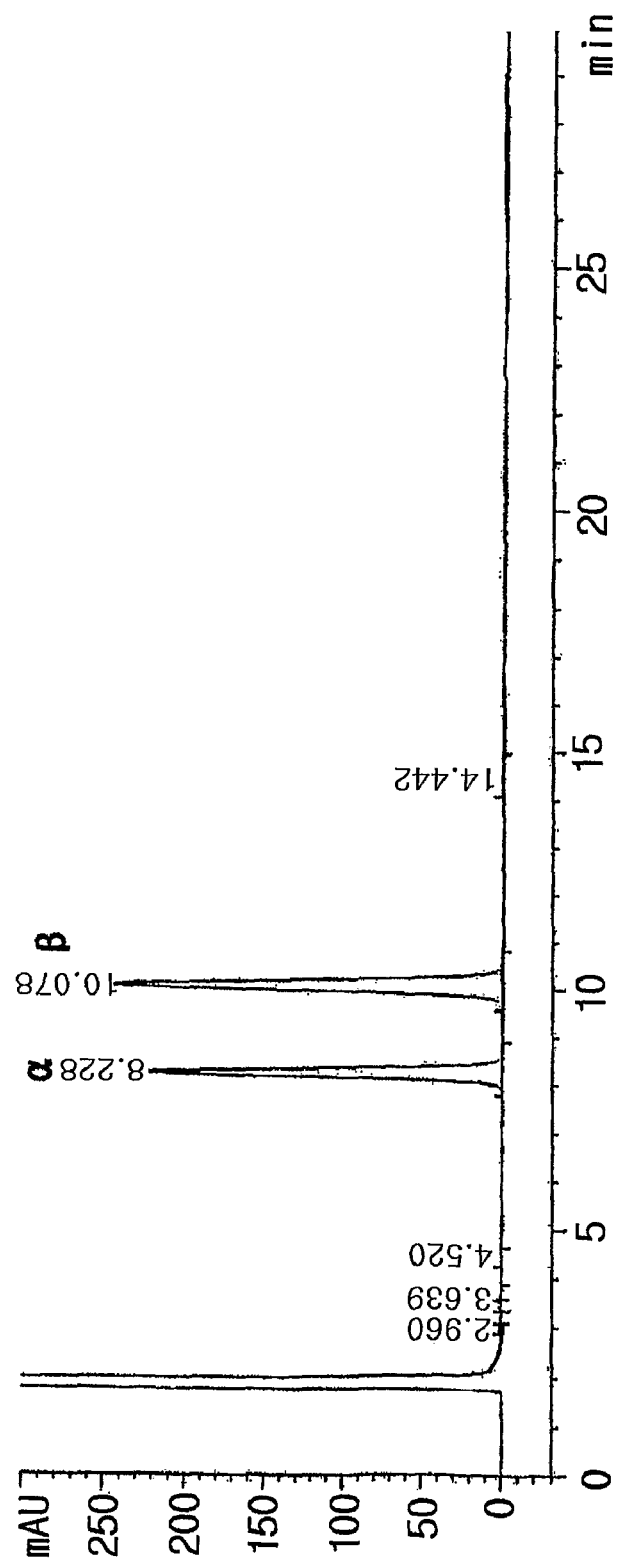

32.2 g of cytosine and 184 mg of ammonium sulfate were added to 184 ml of hexamethyldisilazane. The mixture was refluxed for 1 hour and 250 ml of heptane was added thereto and heated to 135 to 140° C. to distil off unreacted hexamethyldisilazane. 10.0 g of 1-α-bromo-2'-deoxy-2',2'-difluoro-D-ribofuranosyl-5-benzoyl-3-(4-phenyl)benzoate obtained in Preparation 1 and 36.3 ml of anisole were added to the resulting solution. The resulting mixture was allowed to react for 10 hours with refluxing and maintaining the reaction temperature at 135 to 140° C. After completing the reaction, 240 ml of heptane was added to the resulting solution and 11.6 ml of water was slowly added thereto. The solid formed was stirred, filtered, washed with heptane and dried at room temperature, to obtain a mixture of α- and β-nucleoside isomers including unreacted cytosine in the form of a white solid. The nucleoside mixture was examined by HPLC analysis to find that the α-nucleoside:β-nucleoside ratio was 1:1.3 (See FIG. 3). The solid was suspended in 300 ml of methylene chloride and 60 ml of methanol, and refluxed for 2 hours. The resulting mixture was filtered, the filtered solid was washed with a mixture of methylene chloride (150 ml) and methanol (30 ml) and distilled under a reduced pressure, to obtain an α/β mixture of 1-(2'-deoxy-2',2'-difluoro-5-benzoyl-3-(4-phenyl)benzoyl-D-ribofuranosyl-4-aminopyrimidin-2-one. The mixture was added with 200 ml of methanol and 83 ml of 7N-ammonia/methanol solution, and stirred at room temperature overnight. After completing the reaction, the solvent was removed under a reduced pressure, and 80 ml of ethyl acetate and 90 ml of water were added to the residue. The aqueous layer was separated and the ethyl acetate layer was extracted with 40 ml of water. The aqueous layers were combined and washed with 40 ml of ether (×2). The water was distilled off under a reduced pressure until water was left in the amount of 5 times based on the theoretical weight of the desired product, and the residue was heated to 50 to 55° C. and cooled to room temperature with stirring for 2 hours to induce the precipitation of a solid. The precipitated solid was filtered, washed with water and acetone and dried with warm wind overnight, to obtain 1.64 g (yield: 32.3%) of the title compound in the form of a pure white crystal.

Moisture content: 3.5%

H-NMR data and melting point were the same as in Example 3-1.

An anomer ratio (HPLC analysis): α-nucleoside/β-nucleoside=1/1.3

The results of glycosylation and deprotection according to Example 4 and Comparative Examples 1 and 2 were summarized in Table 2.

TABLE 2

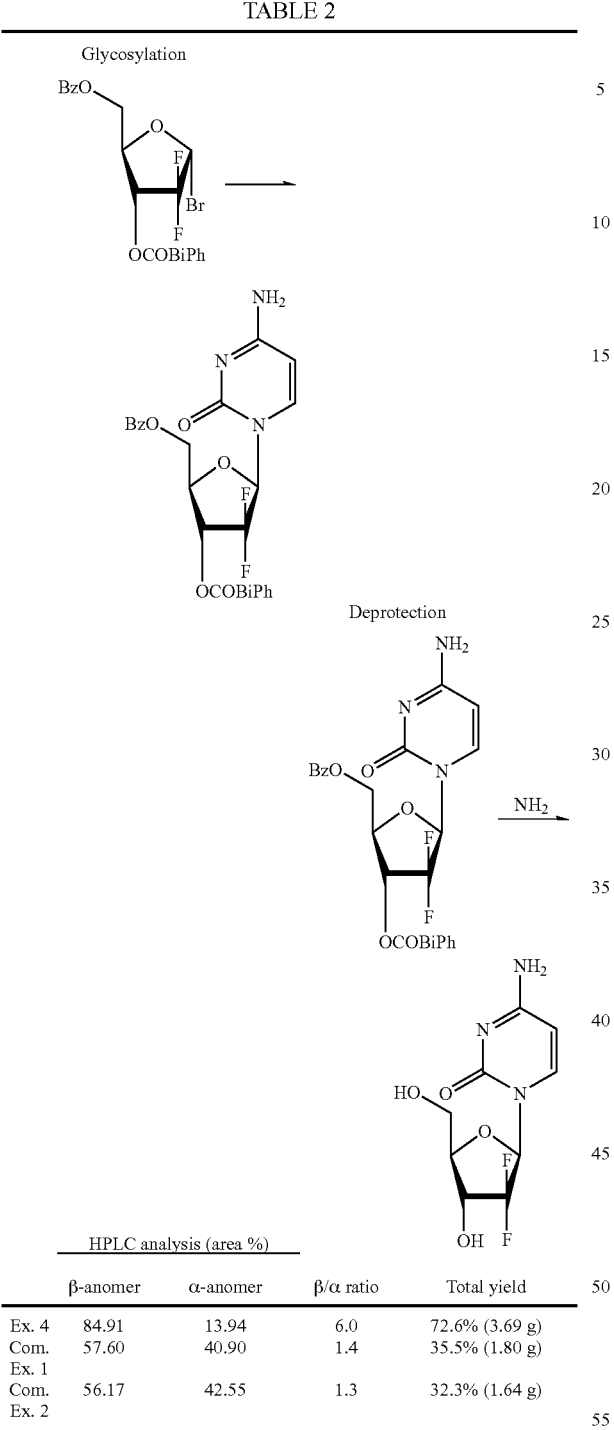

| | HPLC analysis (area %) | | | |
|---|---|---|---|---|
| | β-anomer | α-anomer | β/α ratio | Total yield |
| Ex. 4 | 84.91 | 13.94 | 6.0 | 72.6% (3.69 g) |
| Com. Ex. 1 | 57.60 | 40.90 | 1.4 | 35.5% (1.80 g) |
| Com. Ex. 2 | 56.17 | 42.55 | 1.3 | 32.3% (1.64 g) |

Retention time of the β-anomer peak: 10.08~10.09
Retention time of the α-anomer peak: 8.23

As can be seen from Table 2, in accordance with the present invention, the β-anomer is produced a much higher yield as compared with Comparative Examples 1 and 2.

While the invention has been described with respect to the specific embodiments, it should be recognized that various modifications and changes may be made by those skilled in the art to the invention which also fall within the scope of the invention as defined as the appended claims.

What is claimed is:

1. A method for preparing 2'-deoxy-2',2'-difluorocytidine of formula (I), which comprises the steps of
  (i) reacting a 1-halo ribofuranose compound of formula (III) with a nucleobase of formula (IV) in a solvent to obtain a nucleoside of formula (II) while continuously removing a silyl halide of formula (V) produced during the reaction; and
  (ii) deprotecting the nucleoside of formula (II) by reacting the nucleoside of formula (II) with at least one selected from the group consisting of water, an alcohol, a base, an acid catalyst, and an acidic ion exchange resin to obtain 2'-deoxy-2',2'-difluorocytidine of formula (I):

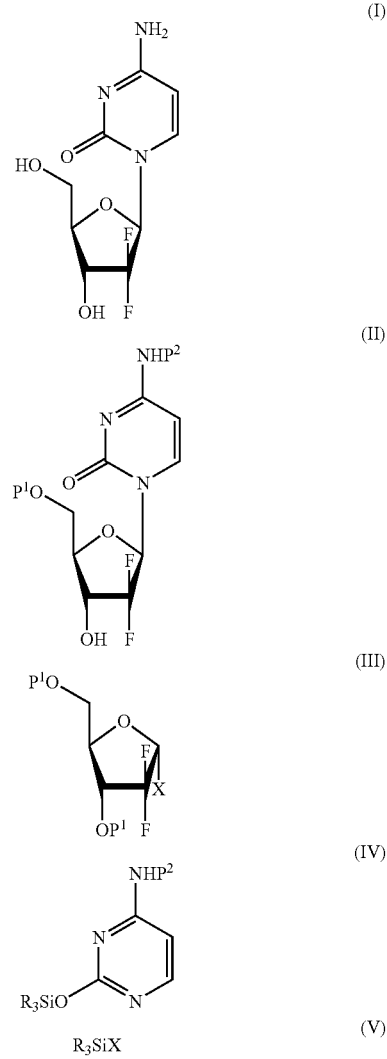

wherein,
R is an alkyl;
$P^1$ is a hydroxy-protecting group;
$P^2$ is an amino-protecting group; and
X is a halogen.

2. The method of claim 1, wherein the removal of the silyl halide in step i) is carried out by distillation.

3. The method of claim 1, wherein the nucleobase of formula (IV) present in step i) is in an amount ranging from 5 to 50 molar equivalents based on 1 molar equivalent of 1-halo ribofuranose of formula (III).

4. The method of claim 1, wherein the solvent present in step i) is selected from the group consisting of benzene, substituted benzene, toluene, xylene, decalin, diglyme, 2-ethoxyethyl ether, diphenylether, substituted diphenylether, biphenyl, substituted biphenyl, $C_{6-14}$ alkane, substituted $C_{6-14}$ alkane and a mixture thereof.

5. The method of claim 1, wherein the silyl halide of formula (V) is trimethylsilylbromide.

6. The method of claim 2, further comprising adding a volatile solvent carrier to a reaction mixture, when the distillation is carried out.

7. The method of claim 6, wherein the carrier is selected from the group consisting of benzene, substituted benzene, toluene, xylene, $C_{6-14}$ alkane, substituted $C_{6-14}$ alkane and a mixture thereof.

8. The method of claim 7, wherein the carrier is heptane.

9. The method of claim 6, wherein the carrier is present in an amount ranging from 50 to 1000 ml based on 1 g of 1-halo ribofuranose.

10. The method of claim 6, further comprising adding a heating medium or N,O-bis(trimethylsilyl)acetamide (BSA) to the reaction mixture, when adding the volatile solvent carrier to the reaction mixture.

11. The method of claim 10, wherein the heating medium is selected from the group consisting of decalin, diphenylether, substituted diphenylether, biphenyl, substituted biphenyl and a mixture thereof.

12. The method of claim 11, wherein the heating medium is diphenylether.

13. The method of claim 10, wherein the heating medium is present in an amount ranging from 0.1 to 5 vol % based on the amount of the carrier.

14. The method of claim 10, wherein N,O-bis(trimethylsilyl)acetamide (BSA) is present in an amount ranging from 0.05 to 1.5 vol % based on the amount of the carrier.

15. The method of claim 1, wherein the removal of the silyl halide in step i) is carried out by passing an inert gas through the reaction mixture.

16. The method of claim 15, wherein the inert gas is selected from the group consisting of nitrogen, helium, neon and argon.

17. The method of claim 15, wherein the inert gas is introduced in the form of bubbling or sweeping.

18. The method of claim 15, wherein the inert gas is introduced at a flow rate of 1 l/min or more based on 100 g of 1-halo ribofuranose of formula (III).

19. The method of claim 1, wherein step i) is carried out at a temperature ranging from 80 to 300° C.

20. The method of claim 1, which in step ii), further comprising after the deprotection, the steps of dissolving the nucleoside of formula (II) in the form of an α/β anomer mixture in water; heating the resulting solution to a temperature of 40 to 60° C.; cooling the solution to a temperature ranging from 10 to 25° C. with or without stirring and without pH-adjustment; and filtering precipitated solids to obtain 2'-deoxy-2',2'-difluorocytidine of formula (I).

21. The method of claim 1 further comprising preparing the hydrochloride salt of 2'-deoxy-2',2'-difluorocytidine of formula (I) by reacting 2'-deoxy-2',2'-difluorocytidine of formula (I) or a hemihydrate or dihydrate thereof with hydrochloric acid in an organic solvent.

* * * * *